United States Patent
Braat

(10) Patent No.: US 6,291,724 B1
(45) Date of Patent: *Sep. 18, 2001

(54) SUPPRESSION OF HIGHLY ALKYLATED PHENOLS IN THE CATALYTIC ALKYLATION REACTION OF PHENOL

(75) Inventor: Adrianus J. F. M. Braat, Selkirk, NY (US)

(73) Assignee: General Electric Company, Pittsfield, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/936,134

(22) Filed: Sep. 24, 1997

(51) Int. Cl.$^7$ .................................................. C07C 37/00
(52) U.S. Cl. .............................................................. 568/804
(58) Field of Search ..................... 568/781, 785, 568/789, 790, 794, 804, 805

(56) References Cited

U.S. PATENT DOCUMENTS

| | | |
|---|---|---|
| 3,417,149 | 12/1968 | Neuworth et al. . |
| 3,998,892 | 12/1976 | Leach . |
| 4,071,566 | 1/1978 | Leach et al. . |
| 4,125,736 | 11/1978 | Leach . |
| 4,191,844 | 3/1980 | Bjornson . |
| 4,230,895 | 10/1980 | Daly . |
| 4,230,896 | 10/1980 | Daly . |
| 4,283,574 * | 8/1981 | Leach .................... 568/804 |
| 4,476,329 * | 10/1984 | Chambers ............... 568/804 |
| 4,533,767 | 8/1985 | Talley . |
| 4,533,768 | 8/1985 | Talley . |
| 4,554,267 * | 11/1985 | Chambers ............... 502/340 |
| 4,554,388 * | 11/1985 | Keim ...................... 568/716 |
| 4,560,810 | 12/1985 | Talley et al. . |
| 4,590,306 * | 5/1986 | Korff ...................... 568/804 |

OTHER PUBLICATIONS

"Hackh's Chemical Dictionary," 4th Ed., p.508, 1969.*
"Catalytic Steam Dealkylation of Alkyl Phenols" Journal of Catalysis 61, 528–532 (1980).

* cited by examiner

Primary Examiner—Michael L. Shippen

(57) ABSTRACT

Selective catalytic reduction of the formation of alkylated phenols by transalkylation of ortho- and para-positions of alkylated phenols is accomplished by reacting ortho- and/or para-alkylated phenols with unreacted alkylated phenols in the presence of a metal oxide selected from the group consisting of Mg, Zn, Fe, V, Ce, Cs, Mn, or combinations thereof. This invention can be easily executed by recycling the alkylated phenols into the normal feed stream of the alkylation reactor.

23 Claims, No Drawings

SUPPRESSION OF HIGHLY ALKYLATED PHENOLS IN THE CATALYTIC ALKYLATION REACTION OF PHENOL

CROSS-REFERENCE TO RELATED APPLICATIONS

Not applicable.

FEDERALLY SPONSORED RESEARCH

Not applicable.

BACKGROUND OF THE INVENTION

This invention relates to a method for suppressing the formation of certain alkylated phenols with one or more alkyl groups by transalkylating the alkyl phenols. More particularly, this invention is directed to a method for transalkylating ortho- and para-alkylated phenols with other phenols in the presence of a metal oxide catalyst by recycling these phenols into the feed stream.

It is often desirable to dealkylate or transalkylate the alkylated phenols obtained from coal tars of coal liquifaction processes to provide more valuable products, such as phenol. In addition, it is often desirable to dealkylate or transalkylate 2,4,6-trimethylphenol (TMP), a co-product in the synthesis of 2,6-xylenol, to more useful alkylated phenols and phenol. Useful alkylated phenols include p-cresol, o-cresol, 2,6-xylenol, 2,4-dimethylphenol, 2,4,6-trimethylphenol and the like.

A number of methods of dealkylating alkylated phenols are known to the art. These methods include thermal dealkylation, thermal hydrodealkylation, and catalytic hydrodealkylation. Thermal dealkylation involves exposing alkylated phenols to high temperatures (about 800° C.) to achieve thermal cracking of the alkylated phenol and yield phenol. However, this process is not selective and a substantial amount of dehydroxylation occurs, producing the less valuable benzene and alkyl-substituted benzene species. This process is shown more particularly by Daly in Journal of Catalysis 61, 528 (1980), the contents of which are incorporated herein by reference.

Thermal hydrodealkylation of alkylated phenols involves exposing the alkylated phenols to high temperatures in the presence of steam or hydrogen or both, as is shown by Daly in U.S. Pat. No. 4,230,895. This process also causes a significant amount of dehydroxylation, which is undesirable since dehydroxylation produces less valuable products.

Catalytic hydrodealkylation is typically more selective than the processes described above and causes less dehydroxylation. Daly describes a process in U.S. Pat. No. 4,230,896 wherein alkylated phenols are reacted with steam in the presence of a catalyst comprised of a hydrous carrier, a deactivation suppressor and at least one promoter. Catalysts included within those described by Daly include platinum and palladium on alumina and mixtures of palladium and chromium oxide on alumina. A catalytic hydrodealkylation process which reacts alkylated phenols with hydrogen is described by Bjornson in U.S. Pat. No. 4,191,844. This reaction takes place in the presence of a catalyst consisting essentially of magnesium oxide and a Group IIA metal oxide such as manganese oxide. Although, these catalytic hydrodealkylation processes are more selective and cause less dehydroxylation than thermal hydrodealkylation, there still remains room for improvement. For example, the percentage of alkylated phenol converted to a new material is very low (about 40%) in the process described in U.S. Pat. No. 4,230,896 and dehydroxylation is still significant, providing 5–30 weight % dehydroxylated products. When the alkylated phenols are reacted with hydrogen in the process described by Bjornson, the rate of dehydroxylation is also high producing large quantities of dehydroxylated products (up to 50 weight %) at high rates of dealkylation. In addition, these processes which utilize a catalyst to dealkylate alkylated phenols are handicapped by the short lifetime of the catalyst due to coking. The catalyst must be reactivated or regenerated periodically and a deactivation suppressant is often necessary.

The disproportion of highly alkylated phenols with phenol over a tungsten oxide promoted magnesium oxide catalyst is described by Leach in U.S. Pat. No. 4,125,736. The catalyst contained 0.5 to 15% tungsten oxide and the reaction was executed with 1 to 15% water resulting in o-cresol and p-cresol as the main products.

An acidic catalyst containing 75–100% aluminum oxide and 0–25% silica for the transmethylation of alkylated phenols in the presence of phenol or cresol is described by Talley in U.S. Pat. No. 3,417,149. Talley in U.S. Pat. No. 4,533,767 describes the steam dealkylation of ortho and or para alkylated phenols without the loss of a hydroxyl radical without phenol present in the feed stream. In U.S. Pat. No. 4,533,786, Talley describes a similar steam dealkylation as described in U.S. Pat. No. 4,533,767, however, using zinc oxide as the main component of the catalyst as opposed to magnesium oxide. In U.S. Pat. No. 4,560,810, Talley describes the ortho dealkylation alkylated hydroxyaromatic compounds using a combination of chromium oxide and one of the oxides of zinc, iron, magnesium, or manganese.

The suppression of the formation of highly alkylated phenols by a catalytic transalkylation process comprising this invention provides high conversion rates, generally on the order of 25 weight percent or higher. In addition, the catalyst lifetime is extended for particular embodiments of this invention so as to reduce the frequency of regeneration.

SUMMARY OF THE INVENTION

A method for the suppression of highly alkylated phenols is provided comprising reacting an alkylated phenol with another phenol in the presence of a metal oxide catalyst, said alkylated phenol having at least one alkyl radical of from 1 to about 6 carbon atoms either ortho-positioned or para-positioned to the hydroxyl radical, and said phenol having at least one position available in the ortho- or para-position with respect to the hydroxyl radical.

An object of the invention is to suppress the formation of the undesired alkylated phenols by transalkylating the alkylated phenols into useful products by recycling these phenols into a normal alkylating feed stream.

Another object of the present invention is to transalkylate alkylated phenols at a high conversion rate without loss of selectivity.

Another object of the present invention is decrease the frequency at which the catalyst must be regenerated when transalkylating alkylated phenols by a catalytic steam transalkylating process.

DESCRIPTION OF THE DRAWINGS

Not applicable.

DETAILED DESCRIPTION OF THE INVENTION

The present invention is directed at the suppression of the formation of certain alkylated phenols by a catalytic transalkylating process that selectively transalkylates the ortho- and para-positioned alkyl groups with respect to the hydroxyl radical of an alkylated phenol. The term "dealkylating" as used herein, refers to the removal of alkyl groups, usually alkyl groups containing 1 to about 6 carbon atoms, from the aromatic nucleus of phenols. The term "transalkylating" as used herein, refers to the shift of the alkyl groups to another position on the aromatic ring within the same molecule or being positioned on the aromatic ring of another phenol. The term "dehydroxylation" as used herein, refers to the loss of the hydroxyl radical on the aromatic nucleus of the phenols.

Suitable alkylated phenols which can be dealkylated or transalkylated by this process include those containing one hydroxyl radical and at least one alkyl group at an ortho- and/or para-position relative to the hydroxyl radical. These alkylated phenols may contain multiple alkyl groups at various positions on the aromatic nucleus and these alkyl groups may be straight chain or branch chain. Examples of suitable alkylated phenols include isomers of cresol, isomers of xylenol, ethyl phenol, n-proylphenol, and isomers of trimethylphenol, etc.; which contain at least one alkyl substituent on a para-, meta-, or ortho-position with respect to the hydroxyl radical. More particularly these include ortho-cresol, para-cresol, 2,4-xylenol, 2,3-xylenol, 2,5-xylenol, 2,6-xylenol, 2,3,4-trimethylphenol, 2,3,5-trimethylphenol, 2,3,6-trimethylphenol, 2,4,6-trimethylphenol, 2,4,5-trimethylphenol, 3,4,5-trimethylphenol, 2-ethylphenol, 4-ethylphenol, 2,4-diethylphenol, etc. The feed of alkylated phenols may be comprised of one single alkylated phenol or a mixture of alkylated phenols; mixtures typically being derived from tar acids obtained from coal liquifaction processes or derived from the alkylating process itself.

Typical reactor feeds for transalkylation reactions comprise an alkyl radical acceptor, defined herein as a phenol having at least one ortho- or para-position vacant (e.g., phenol) and an alkyl radical donor, defined herein as a phenol with at least one alkyl radical at an ortho- or para-position (e.g., 2,4,6-trimethylphenol). The ratio of phenol that has at least one position available in the ortho- or para-position with respect to the hydroxyl radical to alkylated phenols is generally within the range of 1:100 to 100:1. In a preferred embodiment, the ratio of phenol that has at least one position available in the ortho- or para-position with respect to the hydroxyl radical to alkylated phenols is within the range of about 5:1 to about 25:1. A reactor feed may be comprised of one species which satisfies both descriptions, such as o-cresol. These reactions differ from the dealkylation reactions in that the preferred temperature range is lower, typically between about 425° to about 550° C.

The reactor feed may be substantially free of additional solvent or alternatively, the reactor feed may be dissolved in an organic solvent so as to make addition into the reactor easier. Any organic solvent which is inert under dealkylation conditions is suitable, provided it is a good solvent medium for the alkylated phenols and the alkyl radical acceptor. In one preferred embodiment, the reaction is done under normal alkylation conditions wherein methanol and water are present in the feed that can serve the role of the solvent. In another preferred embodiment, the alkyl radical acceptor serves the role of the solvent. In an alternative preferred embodiment, the preferred solvent is selected from the group consisting of benzene, toluene, hexane, and heptane. Other suitable solvents include tetrahydrofuran, chlorobenzene, hexane, etc.

The use of a catalyst comprised of about 60 to about 100 weight % magnesium oxide, about 0 to about 40 weight % manganese oxide and about 0 to about 20 weight % organic binder, preferably polyphenylene oxide, with or without a small amount of a promoter up to 5 weight %, wherein all weight are based upon the weight of the catalyst, provides a high degree of conversion of alkyl radical donors, particularly 2,4,6-trimethylphenol in excess phenol. In a preferred embodiment, the catalyst comprised of about 90 to about 99 weight % magnesium oxide and about 1 to about 5 weight % organic binder, and a small amount, typically about 0.1 weight %, of copper nitrate that acts as a promoter wherein all weight are based upon the weight of the catalyst. Utilizing the normal alkylating conditions and feed stock extends the catalyst lifetime and provides a simple and efficient route to producing, e.g., o-cresol, p-cresol, 2,4-dimethylphenol and 2,6-dimethylphenol from 2,4,6-trimethylphenol.

The reaction between the unreacted and alkylated phenols and steam takes place in the presence of a catalyst comprised of metal oxide selected from the group consisting of Mg, Zn, Fe, V, Ce, Cs, Mn, or various combinations thereof. Any catalytic form of metal oxide is suitable for use in this process. It is preferable that the magnesium oxide within said catalyst fall within the range of about 60 to about 100% by weight, more preferably within the range of about 90 to about 99% by weight, based upon the weight of the catalyst.

These catalysts may have an inert organic or inorganic binder mixed within in order to permit them to be pelletized and easily handled in the process. Such binders may preferably comprise up to about 20 weight %, more preferably up to about 5 weight %, of said catalyst. Suitable organic binders include: polyphenylene oxide, graphite, etc. Silica is an example of a suitable inorganic binder. In one embodiment of the present invention, polyphenylene oxide binders are the most preferred. The catalyst may also contain a promoter, for example, copper nitrate in the range of about 0.1 to about 5 weight %.

Metal oxide catalysts retain their activity for several days with little loss of specific activity. However, over long periods of operation, carbon deposition (coking) gradually decreases that activity. When this occurs, the catalysts can be regenerated by oxidation of the carbon by passing oxygen or air over the catalyst at temperatures in the range of about 400° to 500° C.

An alternative method utilized to retard the coking of the catalyst surface is to introduce an oxidizing atmosphere (oxygen, air, or another oxygen nitrogen mixture) into the reactor via the reactor feed so that the reaction takes place in the presence of this oxidizing atmosphere, which is preferably air.

The rate at which alkylated phenols are fed into the reactor to react with unreacted phenols in the presence of catalyst is not critical to achieve the desired objects of this invention. The flow rate of reactants does effect the product yield by determining the amount of contact time between the alkylated phenol and catalyst. Due to the difference in the specific activities of metal oxide catalysts, each catalyst will have a different optimum flow rate than another. The more active the catalyst, the shorter contact time necessary to produce the same quantity of transalkylated phenols. Therefore, to obtain a particular conversion rate, higher weight hourly space velocities can be used with more active catalysts while lower weight hourly space velocities are necessary with less active catalysts. A flow rate which is too high will flood the catalyst and not permit the reaction to proceed. Where the catalyst utilized contains a promotor within the range of about 0.05 to 5 weight % and an organic binder within the range of about 0 to 20 weight %, a flow rate having a weight hourly space velocity in the range of about 0.1 to 3.0 grams alkylated phenol/hour/grams of catalyst is preferred. The most preferred flow rate is at a weight hourly space velocity of about 0.3 to 1.0 grams of alkylated phenol/hour/grams of catalyst. Both higher and lower flow rates can be utilized with such catalysts.

The starting materials are preferably in the vapor phase when in the presence of the metal oxide catalyst at the operable temperature ranges. To avoid cooling of the catalyst below the reaction temperature selected, it is preferable to vaporize and preheat the starting materials prior to contact with the metal oxide catalyst. To minimize the decomposition of the starting materials, it is most preferable to maintain the starting materials at the minimum temperature necessary to vaporize them and then preheat the starting materials to the reaction temperature immediately prior to contact with the metal oxide catalyst. This can be accomplished by passing the vaporized starting materials through a heated tube of metal or quartz or by passing the vaporized starting materials over heated quartz beads just prior to entry into the catalyst bed. It is preferable to utilize the same heating medium to preheat the vapors which is used to heat the catalyst bed so as to maintain a stable reaction temperature within the reactor.

Both products and unreacted starting materials exit the metal oxide catalyst bed preferably in vapor form and are typically condensed to a liquid for subsequent use. This can be accomplished by any conventional means, such as common air or water condenser. The products are then separated from the condenser effluent, preferably by distillation in a conventional distillation apparatus.

The process can be carried out in a conventional reactor used for vapor phase reactions over a solid catalyst. For example, a tubular reactor of quartz or metal filled with a static bed of metal oxide catalyst is suitable. The reactor is heated to the desired temperature by any conventional means; for example, it can be heated by surrounding the reactor with an electric heater or by surrounding the reactor with a heated gas, liquid, or a fluidized solid medium.

In order that those skilled in the art may better understand this invention, the following experiments are provided by way of explanation and not by way of limitation.

All patents cited herein are incorporated herein by reference.

EXPERIMENTAL

In each of Examples 1 through 4, the following procedure was utilized:

A fluidized sand bath heated containing a U-shaped tubular reactor of 15 cm in length and having a diameter of about 1.2 cm was used with a thermocouple inside to monitor the temperature of the catalyst bed.

The sand bath (enlarged Techne SBL-2) could control the temperature within about +/-5° C. The reactor was filled with the magnesium carbonate catalyst granules (size 700–1000 $\mu$m although different sieve fractions can be used) at the lowest part of the reactor. The catalyst was calcined at about 400° C. for about 21 hours while a nitrogen flow was maintained through the reactor. The reactor was then brought to the desired temperature.

The reactant feed was introduced using a Gipson HPLC pump (type 307) at a rate which provided a WHSV of 0.55, unless indicated otherwise.

The products in the effluent (abbreviated "effl" in the tables) which exited the reactor at the listed times were condensed and analyzed by GLC with a HP5890A chromatograph that was equipped with a HP1 column. The samples were collected and analyzed, at the times as stated in the tables.

The catalyst that was used in the experiments consists of about 97.6 weight % magnesium carbonate, about 2 weight % polyphenylene oxide, about 0.5 weight % graphite, and about 0.1 weight % copper nitrate, with all weights based on the weight of the catalyst. This catalyst was used unless stated otherwise.

Example 1

The feed consists of 18.9 weight % methanol and 27.0 weight % water with the remaining percentage as the phenols (i.e. phenol and 2,4,6-TMP) in the specified ratio. Listed in the table are only the phenol products in the effluent at the specified time.

TABLE 1

|  | WHSV | Temp. | Phenol | o-cresol | p-cresol | 2,6-DMP | 2,4-DMP | 2,4,6-TMP |
|---|---|---|---|---|---|---|---|---|
| Feed |  |  | 50.0 |  |  |  |  | 50.0 |
| effl 2h | 0.86 | 475 | 53.6 | 22.2 | 1.1 | 15.2 | 3.3 | 4.3 |

The totals do not always add up to be 100% because not all products are listed, e.g., anisol, 2-methylanisol, 2-ethylphenol, 2,4,6-trimethylanisol, etc. Example 1 illustrates the opportunity of recycling mesitol (2,4,6-trimethylphenol) together with a normal feed stream of phenol, methanol and water.

Example 2

The feed consists of 48.0 weight % methanol and 16.7 weight % water with the remaining percentage as the phenols (i.e. phenol and 2,4,6-TMP) in the specified ratio. Listed in the table are only the phenol products in the effluent at the specified time.

TABLE 2

|  | WHSV | Temp. | Phenol | o-cresol | p-cresol | 2,6-DMP | 2,4-DMP | 2,4,6-TMP |
|---|---|---|---|---|---|---|---|---|
| Feed #1 |  |  | 95.0 |  |  |  |  | 5.0 |
| effl 50h | 0.55 | 460 | 7.1 | 10.1 | 0.03 | 71.52 | .49 | 9.0 |
| effl 362h | 0.55 | 460 | 15.0 | 10.4 | 0.02 | 65.8 | .23 | 7.9 |
| Feed #2 |  |  | 100.0 |  |  |  |  |  |
| effl 50h | 0.55 | 460 | 8.5 | 10.6 | 0.03 | 69.5 | 0.41 | 9.6 |
| effl 362h | 0.55 | 460 | 19.3 | 20.7 | 0.19 | 50.2 | 1.22 | 7.1 |

A reference reaction was run at the same time in the same sand bath to ensure a good comparison with the same temperature profile.

The reaction with 5% mesitol in the feed from the start showed a somewhat suppressed 2,6-xylenol formation during the first 50 hours but on the other side it also did produce significantly less mesitol. After this period the formation of 2,6-xylenol became normal and even a little higher then the reference reaction. This finally resulted in the formation of 505 grams of 2,6-xylenol versus 372 grams of 2,6-xylenol from the reference reaction.

The amount of mesitol in the effluent after 362 hours was 76 grams and of the reference reaction 78 grams which was the same. But during this time the reaction with 5% mesitol in the feed had fed the reactor with 35 grams of mesitol which means that all of that is transformed to other substances. This leads to the conclusion that approximately 50% of the mesitol formation is suppressed since the net mesitol formation was now 41 grams and the net mesitol production of the reference reaction was 78 grams during the same time.

Example 3

Catalyst: manganese oxide and magnesium oxide is a ratio of 1:3+binder additives The feed consists of 48.0 weight % methanol and 16.7 weight % water with the remaining percentage as the phenols (i.e. phenol and 2,4,6-TMP) in the specified ratio. Listed in the table are only the phenol products in the effluent at the specified time.

TABLE 3

|  | WHSV | Temp. | Phenol | o-cresol | p-cresol | 2,6-DMP | 2,4 DMP | 2,4,6-TMP |
|---|---|---|---|---|---|---|---|---|
| Feed #1 |  |  | 95.0 |  |  |  |  | 5.0 |
| effl 50h | 0.55 | 450 | 33.7 | 47.2 | 0.10 | 13.7 | 0.57 | 4.43 |
| effl 98h | 0.55 | 453 | 56.9 | 35.2 | 0.07 | 2.8 | 0.30 | 4.51 |
| Feed #2 |  |  | 100.0 |  |  |  |  |  |
| effl 50h | 0.55 | 450 | 41.9 | 51.7 | 0.10 | 4.7 | 0.33 | 0.06 |
| effl 98h | 0.55 | 453 | 58.2 | 35.7 | 0.11 | 4.6 | 0.19 | 0.06 |

The effluent composition contained almost over the whole run less than 5 weight % mesitol, which is less than was present in the feed even if the amount is corrected for the molecular weight gain.

Example 4

The feed consists of 48.0 weight % methanol and 16.7 weight % water with the remaining percentage as the phenols (i.e. phenol and 2,4-DMP) in the specified ratio. Listed in the table are only the phenol products in the effluent at the specified time.

TABLE 4

|  | WHSV | Temp. | Phenol | o-cresol | p-cresol | 2,6-DMP | 2,4-DMP | 2,4,6-TMP |
|---|---|---|---|---|---|---|---|---|
| Feed #1 |  |  | 95.0 |  |  | 5.0 |  |  |
| effl 49h | 0.55 | 450 | 11.7 | 28.5 | 0.38 | 44.1 | 3.84 | 10.7 |
| effl 170h | 0.55 | 450 | 2.4 | 16.5 | 0.04 | 68.3 | 1.39 | 10.3 |
| Feed #2 |  |  | 100.0 |  |  |  |  |  |
| effl 49h | 0.55 | 450 | 8.3 | 28.1 | 0.27 | 46.6 | 2.93 | 11.9 |
| effl 170h | 0.55 | 450 | 9.5 | 17.8 | 0.11 | 58.7 | 1.49 | 11.0 |

This reaction shows this technique is not limited to 2,4,6-trimethylphenol but can be applied for other alkylated phenols as well. In this example the same procedure is used for 2,4-dimethylphenol showing again good suppression. Moreover, there was no net formation of 2,4-xylenol which is considered an unwanted by-product in some alkylation reactions.

Although the above Examples have shown various modifications of the present invention, further modifications are possible in light of the above techniques by one skilled in the art without departing from the scope and spirit of this invention.

What is claimed is:

1. A method of suppressing the formation of 2,4-dimethylphenol and/or 2,4,6-trimethylphenol, comprising:
   introducing a first feed stream to a metal oxide catalyst, said first feed stream comprising feed phenol, methanol, and water;
   maintaining the temperature of the catalyst at about 400° C. to about 675° C.,
   introducing into the feed stream an effective amount of 2,4-dimethylphenol and/or 2,4,6-trimethylphenol to suppress the formation of the introduced alkylated phenol(s);
   producing a first effluent stream comprising a mixture of alkylated phenols including 2,4-dimethyphenol and/or 2,4,6-trimethylphenol.

2. A method as in claim 1, wherein production of 2,4,6-trimethylphenol is suppressed approximately 50% when compared to a method without step (c).

3. A method as in claim 1, wherein production of 2,4-dimethyl phenol is suppressed more than 50% when compared to a method without step (c).

4. A method as in claim 1, wherein the metal of the metal oxide catalyst is selected from the group consisting of Mg, Zn, Fe, V, Ce, Cs, Mn, and various combinations thereof.

5. A method as in claim 1, wherein the catalyst is comprised of about 60 to 100 weight % magnesium oxide, about 0 to 40 weight % manganese oxides about 0 to 20 weight % of an organic binder, and 0 to 5 weight % promoter, wherein all the weights are based upon the weight of the catalyst.

6. A method as in claim 5, wherein the catalyst is maintained at a temperature of about 425° to 550° C.

7. A method as in claim 5, wherein said feed stream has a flow rate of about 0.1 to 3.0 grams/hour/gram of catalyst.

8. A method as in claim 1, wherein introducing an effective amount of 2,4-dimethylphenol and/or 2,4,6-trimethylphenol to the first feed stream comprises introducing at least a portion of the formed 2,4-dimethylphenol and/or 2,4,6-trimethylphenol from said first effluent stream to said first feed stream to produce a second effluent stream.

9. A method as in claim 8, further comprising introducing at least a portion of said second effluent stream the catalyst.

10. A method as in claim 8, further comprising dissolving said phenol in a solvent prior to introduction to said catalyst, wherein said solvent is benzene, toluene, hexane, or heptane.

11. A method as in claim 8, wherein said first effluent stream and said second effluent stream comprise 2,4,6-trimethylphenol, and wherein the percent of 2,4,6-trimethylphenol in said second effluent stream is less than the percent of 2,4,6-trimethylphenol in said first effluent stream.

12. A method as in claim 8, wherein said first effluent stream and said second effluent stream comprise 2,4-dimethyl phenol, and wherein the percent of 2,4-dimethyl phenol in said second effluent stream is less than the percent of 2,4-dimethyl phenol in said first effluent stream.

13. A method for producing 2,6-dimethylphenol, while suppressing the formation of 2,4-dimethylphenol and/or 2,4,6-trimethylphenol comprising:
   introducing a first feed stream to a metal oxide catalyst, said first feed stream comprising feed phenol, methanol, and water,
   maintaining the temperature of the catalyst at about 400° C. to about 675° C.;
   introducing an effective amount of 2,4-dimethylphenol and/or 2,4,6-trimethylphenol;
   producing a first effluent stream comprising 2,6-dimethylphenol and including 2,4-dimethylphenol and/or 2,4,6-trimethylphenol.

14. A method as in claim 13, wherein production of 2,4,6-trimethylphenol is suppressed approximately 50% when compared to a method without step (c).

15. A method as in claim 13, wherein production of 2,4-dimethyl phenol is suppressed more than 50% when compared to a method without step (c).

16. A method as in claim 13, further comprising dissolving said phenol in a solvent prior to introduction to said catalyst, wherein said solvent is benzene, toluene, hexane, or heptane.

17. A method as in claim 13, wherein the metal of the metal oxide catalyst is selected from the group consisting of Mg, Zn, Fe, V, Ce, Cs, Mn, and various combinations thereof.

18. A method as in claim 13, wherein the catalyst is comprised of about 60 to 100 weight % magnesium oxide, about 0 to 40 weight % manganese oxide, about 0 to 20 weight % of an organic binder, and 0 to 5 weight % promoter, wherein all the weights are based upon the weight of the catalyst.

19. A method as in claim 18, wherein the catalyst is maintained at a temperature of about 425° to 550° C.

20. A method as in claim 18, wherein said feed stream has a flow rate of about 0.1 to 3.0 grams/hour/gram of catalyst.

21. A method as in claim 13, wherein introducing an effective amount of 2,4-dimethylphenol and/or 2,4,6-trimethylphenol to the first feed stream comprises introducing at least a portion of the formed 2,4-dimethylphenol and/or 2,4,6-trimethylphenol from said first effluent stream to said first feed stream to produce a second effluent stream.

22. A method as in claim 21, further comprising introducing at least a portion of said second effluent stream to the first feed stream.

23. A method as in claim 21, wherein said first effluent stream and said second effluent stream comprise 2,4-dimethyl phenol, and wherein the percent of 2,4-dimethyl phenol in said second effluent stream is less than the percent of 2,4-dimethylphenol in said first effluent stream.

* * * * *